US012797214B2

(12) United States Patent
Li et al.

(10) Patent No.: US 12,797,214 B2
(45) Date of Patent: Nov. 17, 2026

(54) DELIVERY DEVICE, AND INTRAVASCULAR STENT SYSTEM

(71) Applicant: Lifetech Scientific (Shenzhen) Co. Ltd., Shenzhen (CN)

(72) Inventors: Zhen Li, Shenzhen (CN); Benhao Xiao, Shenzhen (CN); Caiping Liu, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 611 days.

(21) Appl. No.: 18/267,716

(22) PCT Filed: Oct. 22, 2021

(86) PCT No.: PCT/CN2021/125595
§ 371 (c)(1),
(2) Date: Jun. 15, 2023

(87) PCT Pub. No.: WO2022/127371
PCT Pub. Date: Jun. 23, 2022

(65) Prior Publication Data
US 2025/0064612 A1 Feb. 27, 2025

(30) Foreign Application Priority Data
Dec. 18, 2020 (CN) ........................ 202011507198.4

(51) Int. Cl.
*A61F 2/95* (2013.01)
*A61F 2/82* (2013.01)

(52) U.S. Cl.
CPC . *A61F 2/95* (2013.01); *A61F 2/82* (2013.01)

(58) Field of Classification Search
CPC ...... A61F 2/07; A61F 2/82; A61F 2/89; A61F 2/90; A61F 2/91; A61F 2/915; A61F 2/95;
(Continued)

(56) References Cited

U.S. PATENT DOCUMENTS

2010/0185271 A1 7/2010 Zhang
2012/0226343 A1* 9/2012 Vo ............................ A61F 2/95 623/1.12
(Continued)

FOREIGN PATENT DOCUMENTS

CN 101779992 A 7/2010
CN 105943215 A 9/2016
(Continued)

OTHER PUBLICATIONS

Search Report dated Oct. 16, 2024 for corresponding European Application No. 21 90 5300.
(Continued)

*Primary Examiner* — Robert A Lynch
(74) *Attorney, Agent, or Firm* — Raymond Sun

(57) ABSTRACT

A delivery device (100) and an intravascular stent (200) system are provided. The delivery device (100) is used for delivering an intravascular stent (200), the intravascular stent (200) including a plurality of corrugated rings (213). The delivery device (100) includes an inner core tube (121), the inner core tube (121) having a loading region (132) for loading the intravascular stent (200). The delivery device (100) further includes at least one positioning member (151) arranged on the inner core tube (121), where the positioning member (151) is located in the loading region (132), and during delivery or release of the intravascular stent (200) by the delivery device (100), the positioning member (151) can axially interfere with at least one of the plurality of corrugated rings (213). The delivery device (100) can prevent axial displacement of the intravascular stent (200) in the loading or release process.

20 Claims, 5 Drawing Sheets

(58) Field of Classification Search
CPC ...... A61F 2/9522; A61F 2/9524; A61F 2/954; A61F 2/958; A61F 2/966; A61F 2002/825; A61F 2002/828; A61F 2002/9155; A61F 2002/91583; A61F 2002/9505; A61F 2002/9511; A61F 2002/9528; A61F 2002/9534; A61F 2002/9583; A61F 2002/9665; A61F 2220/0075
See application file for complete search history.

(56) References Cited

U.S. PATENT DOCUMENTS

| | | | | |
|---|---|---|---|---|
| 2013/0204344 | A1* | 8/2013 | Tatalovich | A61F 2/962 623/1.12 |
| 2014/0257459 | A1 | 9/2014 | Masakazu | |
| 2014/0277332 | A1* | 9/2014 | Slazas | A61F 2/852 623/1.11 |
| 2016/0113793 | A1* | 4/2016 | Nishigishi | A61F 2/95 623/1.11 |
| 2016/0270901 | A1 | 9/2016 | Berra et al. | |
| 2019/0336312 | A1* | 11/2019 | Nageswaran | A61F 2/9662 |

FOREIGN PATENT DOCUMENTS

| | | | |
|---|---|---|---|
| CN | 208725966 | U | 4/2019 |
| CN | 109700572 | A | 5/2019 |
| CN | 209751298 | U | 12/2019 |
| WO | 2018103662 | A1 | 6/2018 |

OTHER PUBLICATIONS

International Search Report dated Jan. 19, 2022 for corresponding PCT Application No. PCT/CN2021/125595.
CN 101779992 A (Achieva Medical (Shanghai) Co., Ltd.) Jul. 21, 2010 (Jul. 21, 2010) description paragraphs 13, 71-86, figures 1-7.
CN 208725966 U (Lifetech Scientific (Shenzhen) Co., Ltd.) Apr. 12, 2019 (Apr. 12, 2019) description, paragraphs 39-59, and figures 1-8.
CN 109700572 A (Lifetech Scientific (Shenzhen) Co., Ltd.) May 3, 2019 (May 3, 2019) description, paragraphs 49-59, and figures 1-7.
CN 105943215 A (Grikin Medical Apparatus and Instruments (Beijing) Co., Ltd. et al.) Sep. 21, 2016 (Sep. 21, 2016) entire document.
CN 209751298 U (Hangzhou Venus Medical Instrument Co., Ltd.) Dec. 10, 2019 (Dec. 10, 2019) entire document.
US 2012226343 A1 (Stryker NV Operations LTD. et al.) Sep. 6, 2012 (Sep. 6, 2012) entire document.
Office Action dated Mar. 13, 2025 for corresponding China Application No. 202011507198.4 and translation.
Second Office action dated Oct. 20, 2025 in corresponding China Appl. No. 202011507198.4.
Office action dated Nov. 11, 2025 in corresponding India Appl. No. 202317048101.

* cited by examiner

DELIVERY DEVICE, AND INTRAVASCULAR STENT SYSTEM

TECHNICAL FIELD

The present disclosure relates to the technical field of interventional medical instruments, and more particularly relates to a delivery device and an intravascular stent system.

BACKGROUND

In recent years, the use of an interventional therapy for cardiovascular disease has become an important means to cure patients. The interventional therapy has low cost, short treatment time, and less trauma to a human body, and has gradually become the mainstream for treating cardiovascular disease. The normal loading, delivery and safe release of an implant (such as a covered stent) by a delivery device play an important role in the success of surgery.

In the prior art, a delivery device includes an end socket, a sheath core tube, a push rod, an outer sheath catheter and a handle assembly. A proximal end of the sheath core tube is fixedly connected with the handle assembly, and a distal end of the sheath core tube is fixedly connected with the end socket. The length of the push rod is less than that of the sheath core tube, and a proximal end of the push rod is fixedly connected with a handle. The length interval between a distal end portion of the push rod and a proximal end portion of the end socket is a loading region for a covered stent. The handle assembly is connected with the outer sheath catheter and can drive the outer sheath catheter to move axially relative to the sheath core tube, thus loading or releasing the covered stent. During the loading of the covered stent, the covered stent is radially compressed between the outer sheath catheter and the sheath core tube in the loading region. During the release of the covered stent, the outer sheath catheter is withdrawn relative to the sheath core tube. Because of an extremely large friction force between the covered stent and the outer sheath catheter, the covered stent is easily driven by the outer sheath catheter to have a large displacement.

SUMMARY

The technical problem to be solved in the present disclosure is to provide a delivery device for the drawback in the prior art that during release of an implant, the implant is easily driven to have a large displacement.

The technical solution used by the present disclosure to solve the technical problems is as follows:

One embodiment of the present disclosure provides a delivery device that is used for delivering an intravascular stent. The intravascular stent includes a plurality of corrugated rings. The delivery device includes an inner core tube, the inner core tube having a loading region for loading the intravascular stent. The delivery device further includes at least one positioning member arranged on the inner core tube. The positioning member is located in the loading region, and during delivery or release of the intravascular stent by the delivery device, the positioning member can axially interfere with at least one of the plurality of corrugated rings.

In one embodiment of the present disclosure, the positioning member is a rigid member.

In one embodiment of the present disclosure, the corrugated ring that is closest to a proximal end of the inner core tube in the intravascular stent is a proximal corrugated ring;

the corrugated ring that is farthest from a distal end of the inner core tube in the intravascular stent is a distal corrugated ring; a plurality of positioning members are provided; at least one of the plurality of positioning members can axially interfere with the distal corrugated ring; and at least one of the plurality of positioning members can axially interfere with the proximal corrugated ring.

In one embodiment of the present disclosure, at least one of the plurality of positioning members is located on a proximal side of the distal corrugated ring and can axially interfere with the distal corrugated ring; and at least one of the plurality of positioning members is located on a distal side of the proximal corrugated ring and can axially interfere with the proximal corrugated ring.

In one embodiment of the present disclosure, the positioning member has a wall thickness S, $0.05 \text{ mm} \leq S \leq 0.8 \text{ mm}$.

In one embodiment of the present disclosure, a clearance is reserved between two adjacent corrugated rings of the intravascular stent; the positioning member is located between two adjacent corrugated rings; and the maximum axial length of the positioning member is equal to the clearance between the two adjacent corrugated rings, or the maximum axial length of the positioning member is less than the clearance between the two adjacent corrugated rings.

In one embodiment of the present disclosure, the central angle corresponding to a proximal end portion and/or a distal end portion of the positioning member is less than 360°.

In one embodiment of the present disclosure, the positioning member is a ring component; and in a projection plane perpendicular to a central axis of the inner core tube, the central angle corresponding to a projection of the positioning member is $\alpha$, $180° < \alpha < 360°$.

In one embodiment of the present disclosure, the positioning member is a ring component, and at least one concave structure is arranged on an outer surface of the positioning member.

In one embodiment of the present disclosure, a plurality of concave structures are provided and arranged along a circumferential direction of the positioning member.

In one embodiment of the present disclosure, the positioning member is spiral along an axial direction of the inner core tube; and the spiral width of the positioning member is H, and the clearance between two adjacent corrugated rings of the intravascular stent is A, $H \leq A$.

In one embodiment of the present disclosure, an intravascular stent system is provided, which includes an intravascular stent and the above delivery device.

When the above delivery device is used, the intravascular stent moves easily axially under the action of an axial external force in the loading or release process, so that the positioning member is located in the loading region. During delivery or release of the intravascular stent by the delivery device, the positioning member axially interferes with at least one of the plurality of corrugated rings, which can prevent the intravascular stent from being driven by an outer sheath catheter to have a large displacement.

BRIEF DESCRIPTION OF THE DRAWINGS

The present disclosure is further described below with reference to the accompanying drawings and embodiments. Among the drawings.

DETAILED DESCRIPTION OF THE DISCLOSURE

In order to make the foregoing objectives, features and advantages of the present disclosure more obvious and understandable, the specific implementation modes of the present disclosure are described in detail with reference to the accompanying drawings. Many specific details are described in the following descriptions to facilitate full understanding of the present disclosure. However, the present disclosure can be implemented in a variety of other ways than those described herein, and those skilled in the art can make similar improvements without departing from the connotation of the present disclosure. Therefore, the present disclosure is not limited by specific implementations disclosed below.

It should be noted that when an element is referred to as being "fixed" or "arranged" to another element, it can be directly on another element, or an intermediate element may also exist. When one element is considered to be "connected" to another element, it can be directly connected to another element or an intermediate element may also exist at the same time. The terms "perpendicular", "horizontal", "left", "right" and similar expressions used herein are for illustrative purposes only, and are not meant to be the only implementation modes.

The "proximal end" in the present application refers to an end closer to an operator, and the "distal end" refers to an end farther from the operator.

Unless otherwise defined, all technical and scientific terms used herein are the same as meanings of general understandings of those skilled in the art of the present disclosure. The terms used in the description of the present disclosure herein are merely to describe the specific implementation modes, not intended to limit the present disclosure. The term "and/or" used herein includes any and all combinations of one or more related listed items.

First Embodiment

Figure 1:
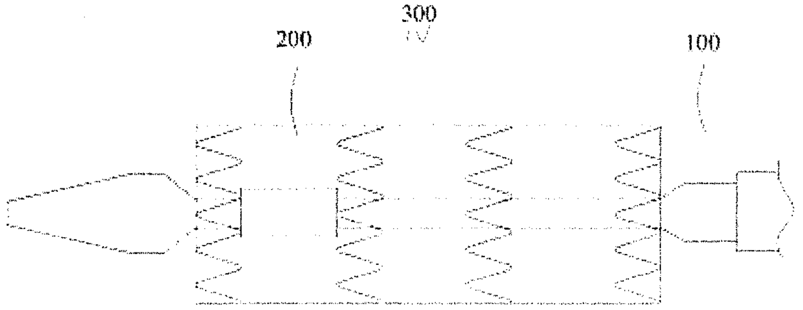
FIG. 1 is a schematic structural diagram of an intravascular stent system according to a first embodiment of the present disclosure.

Referring to FIG. 1, this embodiment provides a delivery device 100 that is used for delivering an intravascular stent 200. The intravascular stent 200 in this embodiment may be a bare stent or a covered stent. The bare stent refers to an intravascular stent 200 formed by axially connecting a plurality of corrugated rings (such as Z-shaped corrugated rings and W-shaped corrugated rings). The plurality of corrugated rings are axially connected through mutual hooking or by means of intermediate connectors. The covered stent refers to an intravascular stent 200 formed by coating a bare stent with a material capable of isolating blood flow. The material capable of isolating blood flow may be a highly bio-compatible material such as polytetrafluoroethylene (PTFE) and polyethylene terephthalate (PET). Furthermore, the material capable of isolating blood flow can also be used as an intermediate connector for connecting a plurality of corrugated rings.

Figure 2:
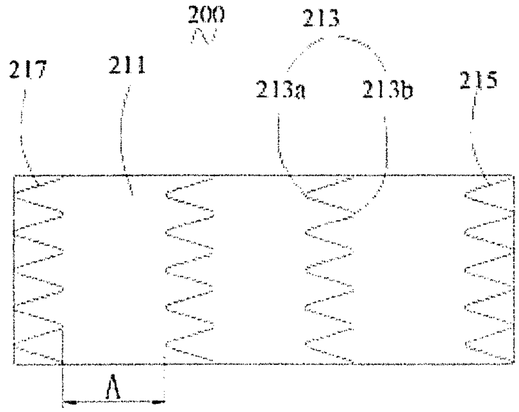
FIG. 2 is a schematic structural diagram of an intravascular stent according to the first embodiment of the present disclosure.

Referring to FIG. 2, the intravascular stent 200 in the embodiment shown in the figure is a covered stent, including a covering film 211 and a plurality of axially connected corrugated rings 213. The plurality of corrugated rings 213 are connected by the covering film 211, and a clearance A is reserved between two adjacent corrugated rings. It should be noted that the clearance A between two adjacent corrugated rings means an axial distance between portions of two adjacent corrugated rings that are closest to each other along an axial direction of the intravascular stent 200. Any corrugated ring 213 has a wave crest **213*a* and a wave trough 213*b*. It can be understood that in this embodiment, a covered stent serving as the intravascular stent 200** is taken as an example for description, but it is not limited to this.

The corrugated ring that is closest to a proximal end of the intravascular stent 200 is a proximal corrugated ring 215, and the corrugated ring that is closest to a distal end of the intravascular stent 200 is a distal corrugated ring 217.

Figure 3:
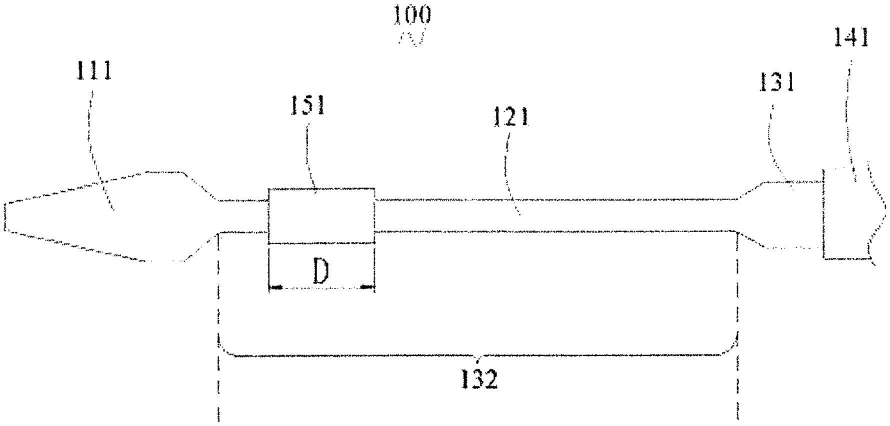
FIG. 3 is a schematic structural diagram of a delivery device according to the first embodiment of the present disclosure.

Referring to FIG. 3, the delivery device 100 includes an end socket 111, an inner core tube 121, a push rod 131, an outer sheath catheter 141 and a positioning member 151.

Specifically, the end socket 111 is located at the distal end of the delivery device 100. The distal end of the end socket 111 is tapered, and the outer diameter of the distal end of the end socket 111 gradually decreases along a direction from the proximal end to the distal end, so that the end socket 111 can easily enter a blood vessel via percutaneous puncture. An outer diameter of the proximal end of the end socket 111 gradually increases along the direction from the proximal end to the distal end. After the delivery device 100 releases the intravascular stent 200 to a target site, when the delivery device 100 is withdrawn, the movement of the intravascular stent 200 due to mutual hooking between the proximal end of the end socket 111 and the distal end of the intravascular stent 200 can be avoided.

The distal end of the inner core tube 121 is connected with the end socket 111. The inner core tube 121 may be made of nickel-titanium alloy, stainless steel or other metal materials, and a guide wire can pass through a tube cavity of the inner core tube 121. Of course, in other embodiments, the material of the inner core tube may also be a polymer material such as polyimide (PI) and polyether ether ketone (PEEK).

The push rod 131 has a tubular structure, which surrounds the inner core tube 121. The push rod 131 is fixedly connected with the inner core tube 121. An inner wall of the push rod 131 is fitted to an outer wall of the inner core tube 121, which can reduce an outer diameter of the outer sheath catheter 141 and facilitate access to blood vessels with smaller inner diameters. It should be noted that the inner wall of the push rod 131 is fitted to the outer wall of the inner core tube 121, which may mean that the push rod 131 is fitted to the inner core tube 121 after they are connected by an intermediate connector (such as glue). The inner wall of the push rod 131 is fitted to the outer wall of the inner core tube 121, which may also mean that they are fused after being integrally formed (such as by injection molding and hot melting). In addition, in other embodiments, a radial clearance may also be provided between the inner wall of the push rod 131 and the outer wall of the inner core tube 121.

The distal end of the push rod 131 is located on the proximal side of the distal end of the inner core tube 121, so that there is an axial clearance between the distal end of the push rod 131 and the proximal end of the end socket 111. Further, the inner core tube 121 forms a loading region 132 for the intravascular stent 200 within a longitudinal interval corresponding to the axial clearance. When the intravascular stent 200 is loaded in the loading region 132, the proximal end of the intravascular stent 200 can abut against the distal end of the push rod 131. Before the distal corrugated ring 217 is released, the displacement of the intravascular stent 200 during the release can be avoided.

The outer sheath catheter 141 slidably surrounds the inner core tube 121 and the push rod 131. When the outer sheath catheter 141 slides to the distal end of the delivery device 100 until it abuts against the proximal end of the end socket 111, the loading region 132 can be closed, and the intravascular stent 200 loaded in the loading region 132 can be radially compressed. When the outer sheath catheter 141 slides to the proximal end of the delivery device 100 until it is completely disengaged with the loading region 132, the intravascular stent 200 can expand radially and be released into a lumen of a blood vessel.

At least one positioning member 151 is provided in this embodiment. The positioning member 151 is a ring component. The positioning member 151 is arranged on the inner core tube 121, and the positioning member 151 is located in the loading region 132. During the delivery or release of the intravascular stent 200 by the delivery device 100, the positioning member 151 can axially interfere with at least one of the plurality of corrugated rings 213. For example, during the delivery or release of the intravascular stent 200 by the delivery device 100, the positioning member 151 may axially interfere with the distal corrugated ring 217, or the positioning member 151 may axially interfere with the proximal corrugated ring 215, or the positioning member 151 may axially interfere with the corrugated rings 213 between the distal corrugated ring 217 and the proximal corrugated ring 215. It should be noted that "the positioning member 151 axially interferes with at least one of the plurality of corrugated rings 213" means that when the intravascular stent 200 is delivered by the delivery device 100 (that is, after the intravascular stent 200 is loaded and before the intravascular stent 200 is released), the positioning member 151 axially interferes with at least one of the corrugated rings 213, or may also be that during the release of the intravascular stent 200, after the intravascular stent 200 is moved for a certain distance, the positioning member 151 axially interferes with at least one of the plurality of corrugated rings 213. In other words, when the intravascular stent 200 is delivered by the delivery device 100, the positioning member 151 can have a clearance from the "at least one of the plurality of corrugated rings 213". After the intravascular stent 200 is moved for a certain distance, the corrugated rings of the intravascular stent 200 axially interfere with the positioning member 151. It should also be noted that the axial interference in this embodiment may be axial abutment. Specifically, the positioning member 151 can axially abut against any other position of the corrugated ring, such as a wave crest, a wave trough, and a wave rod.

In this embodiment, the positioning member 151 is fixed on the inner core tube 121 through the use of glue. The positioning member 151 abuts against a wave trough of the distal corrugated ring 217 on the proximal side of the distal corrugated ring 217. In other embodiments, the positioning member 151 may also be welded on the inner core tube 121 by laser.

Since the intravascular stent 200 has a self-expanding ability, there is a large friction force between the inner wall of the outer sheath catheter 141 and the intravascular stent 200. The outer sheath catheter 141 moves axially relative to the inner core tube 121, which will drive the intravascular stent 200 to move axially. Since the positioning member 151 axially interferes with at least one of the plurality of corrugated rings during the delivery or release of the intravascular stent 200 by the delivery device 100, such the following phenomena can be avoided: that the intravascular stent 200 is driven to move by the outer sheath catheter 141, or the intravascular stent 200 moves excessively.

In this embodiment, the positioning member 151 is a rigid member. During the loading or release of the intravascular stent 200, the rigid positioning member 151 can ensure that the positioning member 151 does not easily deform, making the positioning member 151 resist the corrugated ring more stably, and ensuring that the corrugated ring will not axially cross the positioning member 151 and fall off. Especially when this positioning member is applied to the small-sized outer sheath catheter 141 (for example, when the size of the outer sheath catheter 141 is 7 F to 12 F), since a radial clearance between the outer sheath catheter 141 and the inner core tube 121 is small, in order to load the intravascular stent 200, it is necessary to make the radial size of the positioning member 151 smaller. If the positioning member 151 is rigid, the positioning member 151 can have a stable structural shape (which is not easy to deform), thus improving the reliability of the axial interference of the positioning member 151 with the corrugated ring, so as to ensure that the intravascular stent 200 does not axially move easily when the outer sheath catheter 141 is moved. In this embodiment, the positioning member 151 is a rigid member, which means that the positioning member 151 will not deform under an axial force of 30 N.

The positioning member 151 is a tubular component. In the embodiment shown in the figure, the central angle corresponding to a proximal end portion of the positioning member 151 is 360°, and the central angle corresponding to a distal end portion the positioning member 151 is 360°. The tubular wall of the positioning member 151 is complete and continuous, and the central angle corresponding to any radial plane of the positioning member 151 is 360°. The positioning member 151 has a wall thickness S, 0.05 mm≤S≤0.8 mm, which can be applied to a delivery device 100 with a small-sized outer sheath catheter 141.

In this embodiment, the positioning member 151 is located between two adjacent corrugated rings. The maximum axial length D of the positioning member 151 is equal to the length of the clearance A between the two adjacent corrugated rings, so that two axial ends of the positioning member 151 axially interfere with one corrugated ring respectively, and the delivery device 100 can prevent the intravascular stent 200 from moving both towards the distal end and the proximal end.

In other embodiments, the maximum axial length D of the positioning member 151 may also be less than the length of the clearance A between two adjacent corrugated rings, so that the inner core tube 121 can more easily enter a curved or twisted blood vessel.

Second Embodiment

Figure 4:
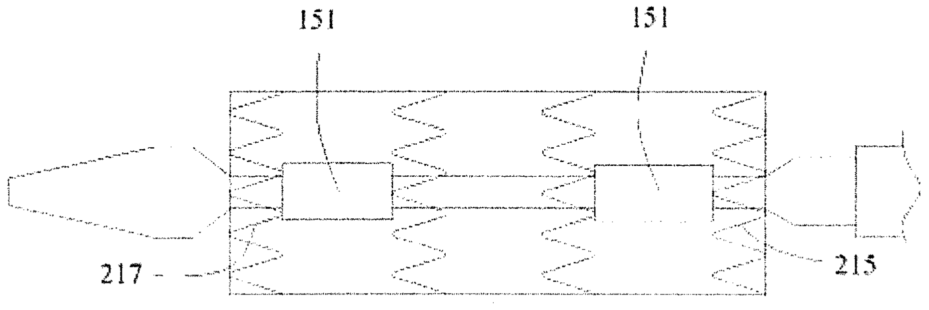
FIG. 4 is a schematic structural diagram of an intravascular stent system according to a second embodiment of the present disclosure.

Referring to FIG. 4, a difference between this embodiment and the first embodiment is that there are a plurality of positioning members 151. At least one of the plurality of positioning members 151 axially interferes with the distal corrugated ring 217, and at least one of the plurality of positioning members 151 axially interferes with the proximal corrugated ring 215, which can prevent movement of the intravascular stent 200 to the distal side and movement of the intravascular stent 200 to the proximal side. Furthermore, the overall intravascular stent 200 will neither be lengthened nor be shortened.

Specifically, at least one of the plurality of positioning members 151 is located on a proximal side of the distal corrugated ring 217 and can axially interfere with the distal corrugated ring 217, and at least one of the plurality of positioning members 151 is located on a distal side of the proximal corrugated ring 215 and can axially interfere with the proximal corrugated ring 215.

In the embodiment shown in the figure, there are two positioning members 151. One positioning member 151 axially interferes with the distal corrugated ring 217, and the other positioning member 151 axially interferes with the proximal corrugated ring 215.

In other embodiments, some positioning members 151 may be located in the middle of the intravascular stent 200 and axially interfere with the corrugated rings between the distal corrugated ring 217 and the proximal corrugated ring 215.

In other embodiments, the number of the positioning members 151 is one less than the number of the corrugated rings 213. Except for the proximal corrugated ring 215 or the distal corrugated ring 217, other corrugated rings all axially interfere with one positioning member 151. That is, except for the proximal corrugated ring 215 or the distal corrugated ring 217, each corrugated ring 213 corresponds to one positioning member 151 and axially interferes with the positioning member 151. In addition, all the positioning members 151 are located on the distal side of the proximal corrugated ring 215, and all the positioning members 151 are located on the proximal side of the distal corrugated ring 217.

Third Embodiment

Figure 5:
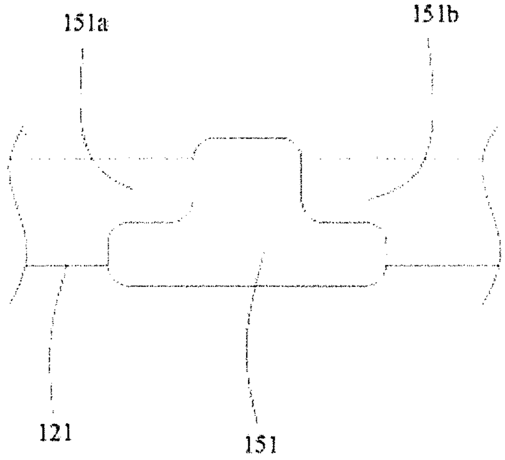
FIG. 5 is a schematic structural diagram of an inner core tube and a positioning member according to a third embodiment of the present disclosure.
Figure 6:
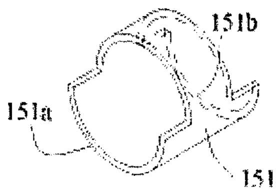
FIG. 6 is a schematic structural diagram of the positioning member according to the third embodiment of the present disclosure.

Referring to FIG. 5 and FIG. 6, a difference between this embodiment and the first embodiment is that the central angle corresponding to the proximal end portion 151*a* of the positioning member 151 is less than 360°, and the central angle corresponding to the distal end portion 151*b* of the positioning member 151 is less than 360°. Thus, boundary lines of the end portions of the positioning member 151 are extended, which is conducive to applying glue and improving the reliability of fixing of the positioning member 151 on the inner core tube 121.

In other embodiments, the central angle corresponding to the proximal end portion 151*a* or the distal end portion 151*b* of the positioning member 151 may be less than 360°.

Fourth Embodiment

Figure 7:
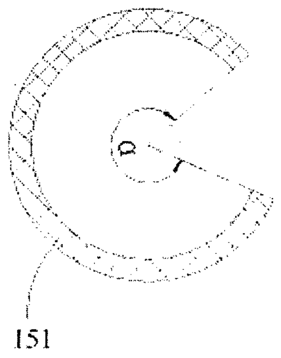
FIG. 7 is a schematic structural diagram of a positioning member according to a fourth embodiment of the present disclosure.

Referring to FIG. 7, a difference of this embodiment is that in a projection plane perpendicular to a central axis of the positioning member 151, a central angle corresponding to a projection of the positioning member 151 is $\alpha$, $180° < \alpha < 360°$, so that any cross section of the positioning member 151 is roughly C-shaped, which can add positions for applying glue and prevent the positioning member 151 from falling off radially. It should be noted that the cross section in this embodiment is a cross section formed by cutting the positioning member 151 along a direction perpendicular to the axis of the positioning member 151.

Fifth Embodiment

Figure 8:
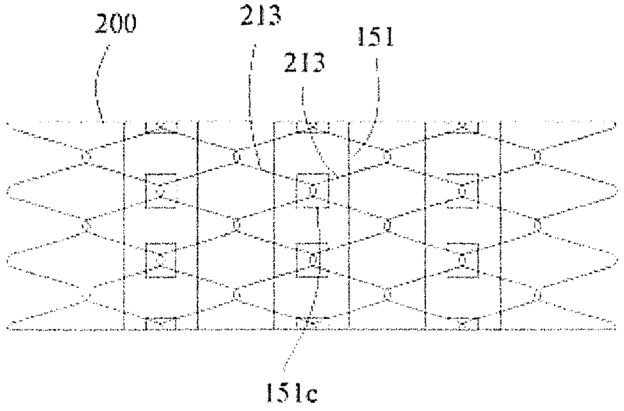
FIG. 8 is a schematic structural diagram showing the cooperation between an intravascular stent and a positioning member according to a fifth embodiment of the present disclosure.
Figure 9:
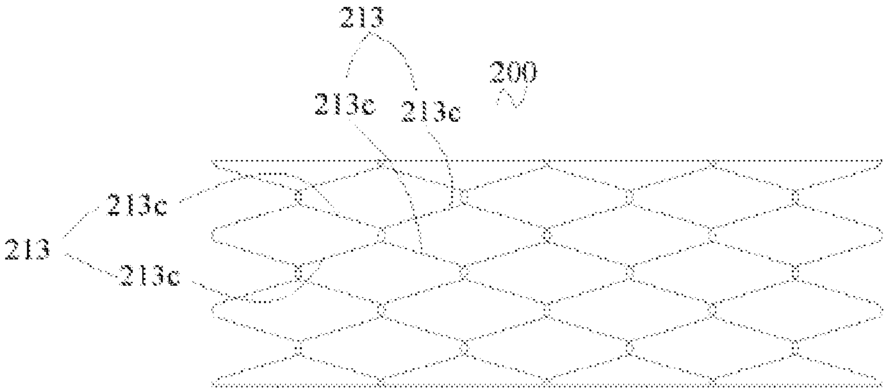
FIG. 9 is a schematic structural diagram of the intravascular stent according to the fifth embodiment of the present disclosure.

Referring to FIG. 8 and FIG. 9 together, the intravascular stent 200 in this embodiment includes a plurality of axially arranged corrugated rings 213. Any corrugated ring 231 includes a plurality of wave rods 231*c* connected at an included angle. One corrugated ring 213 of two adjacent corrugated rings 213 is hooked to the other corrugated ring 213. At least part of the wave rods 213*c* of two hooked corrugated rings 213 overlap radially. One of two wave rods 213*c* that overlap radially is located on an outer side, and the other wave rod 213*c* is located on an inner side.

Figure 10:
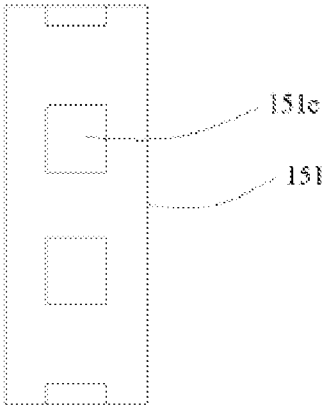
FIG. 10 is a schematic structural diagram showing the cooperation of the positioning member according to the fifth embodiment of the present disclosure.

Referring to FIG. 8 and FIG. 10 together, a difference of this embodiment is that the positioning member 151 is a ring component. A central angle corresponding to the positioning member 151 is 360°. At least one concave structure 151*c* is arranged on the positioning member 151. The concave structure 151*c* is a groove or a through hole. In use, the groove structure is radially aligned with the two wave rods 213*c* that overlap radially. Under the action of a radial pressure of the outer sheath catheter 141, the wave rod located on the outer side can press the wave rod 213*c* that radially overlaps it and is located on the inner side into the concave structure 151*c*, so that the concave structure 151*c* can axially interfere with the intravascular stent 200 and prevent the intravascular stent 200 from axially moving.

In this embodiment, there are a plurality of concave structures 151*c*, and the plurality of concave structures 151*c* are arranged along a circumferential direction of the positioning member 151.

Sixth Embodiment

Figure 11:
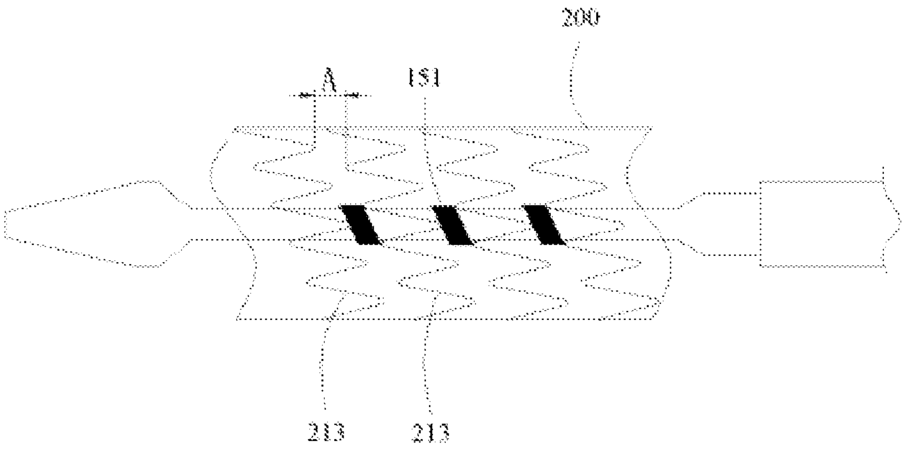
FIG. 11 is a schematic structural diagram of an intravascular stent system according to a sixth embodiment of the present disclosure.
Figure 12:
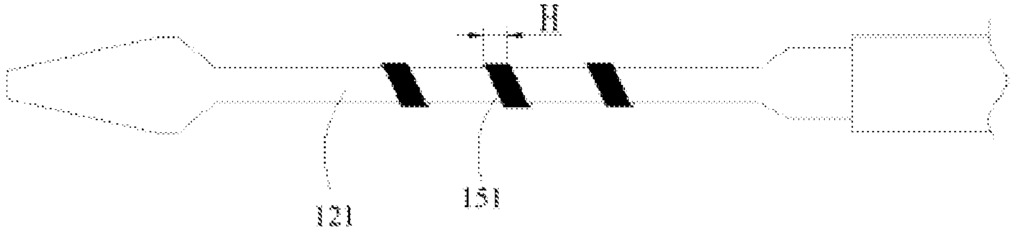
FIG. 12 is a schematic structural diagram of a delivery device according to the sixth embodiment of the present disclosure.

Referring to FIG. 11 and FIG. 12 together, a difference of this embodiment is that in an axial direction of the intravascular stent 200, the corrugated rings 213 extend spirally, and the positioning member 151 extends spirally along the axial direction of the inner core tube 121. The spiral width of the positioning member 151 is H, and the clearance between two adjacent corrugated rings 213 of the intravascular stent 200 is A, H=A, so that the positioning member 151 is embedded into the clearance between two adjacent corrugated rings 213 of the intravascular stent 200, thereby preventing the intravascular stent 200 from axially moving. It should be noted here that the positioning member 151 fixed on the inner core tube 121 can be cut along a direction parallel to the axial direction of the inner core tube 121, and an axial length of a cross section of the positioning member 151 is the spiral width H.

Of course, in other embodiments, H<A can improve the flexibility of the inner core tube 121, making it easier for the inner core tube to enter a curved or twisted blood vessel.

Seventh Embodiment

Referring to FIG. 1, this embodiment provides an intravascular stent system 300, including the above-mentioned intravascular stent 200 and a delivery device which can deliver the intravascular stent 200.

The technical features of the embodiments described above can be arbitrarily combined. In order to make the description concise, all possible combinations of various technical features in the above embodiments are not completely described. However, the combinations of these technical features should be considered as the scope described in this description as long as there is no contradiction in them.

The above-mentioned embodiments only express several implementation modes of the present disclosure, and their descriptions are more specific and detailed, but they cannot be understood as limiting the patent scope of the present disclosure. It should be noted that those of ordinary skill in the art can further make various transformations and improvements without departing from the concept of the present disclosure, and these transformations and improvements all fall within the protection scope of the present disclosure. Therefore, the protection scope of the patent of the present disclosure shall be subject to the appended claims.

The invention claimed is:

1. A delivery device, used for delivering an intravascular stent, the intravascular stent comprising a plurality of corrugated rings; the delivery device comprising an inner core tube, the inner core tube having a loading region for loading the intravascular stent, wherein the delivery device further comprises at least one positioning member arranged on the inner core tube; the positioning member is located in the loading region; and during delivery or release of the intravascular stent by the delivery device, the positioning member axially interferes with at least one of the plurality of corrugated rings;

wherein the positioning member is spiral along an axial direction of the inner core tube; the spiral width of the positioning member is H, a clearance is reserved between two adjacent corrugated rings of the intravascular stent, and the clearance between two adjacent corrugated rings of the intravascular stent is A, with H≤A; and wherein the positioning member is embedded into the clearance between two adjacent corrugated rings.

2. The delivery device according to claim 1, wherein the positioning member is a rigid member.

3. The delivery device according to claim 2, wherein the positioning member will not deform under an axial force of 30 N.

4. The delivery device according to claim 1, wherein the corrugated ring that is closest to a proximal end of the inner core tube in the intravascular stent is a proximal corrugated ring; the corrugated ring farthest from a distal end of the inner core tube in the intravascular stent is a distal corrugated ring; a plurality of positioning members are provided; at least one of the plurality of positioning members axially interferes with the distal corrugated ring; and at least one of the plurality of positioning members axially interferes with the proximal corrugated ring.

5. The delivery device according to claim 4, wherein at least one of the plurality of positioning members is located on a proximal side of the distal corrugated ring and axially interferes with the distal corrugated ring; and at least one of the plurality of positioning members is located on a distal side of the proximal corrugated ring and axially interferes with the proximal corrugated ring.

6. The delivery device according to claim 5, wherein the number of the positioning members is one less than the number of the corrugated rings; and except for the proximal corrugated ring or the distal corrugated ring, other corrugated rings all axially interfere with one positioning member.

7. The delivery device according to claim 1, wherein the positioning member has a wall thickness S, 0.05 mm≤S≤0.8 mm.

8. The delivery device according to claim 1, wherein a maximum axial length of the positioning member is equal to the clearance between the two adjacent corrugated rings, or the maximum axial length of the positioning member is less than the clearance between the two adjacent corrugated rings.

9. The delivery device according to claim 1, wherein a central angle corresponding to a proximal end portion and/or a distal end portion of the positioning member is less than 360°.

10. The delivery device according to claim 9, wherein the central angle corresponding to any radial plane of the positioning member is 360°.

11. The delivery device according to claim 1, wherein the positioning member is a ring component; and in a projection plane perpendicular to the central axis of the inner core tube, the central angle corresponding to a projection of the positioning member is $\alpha$, $180° < \alpha < 360°$.

12. The delivery device according to claim 1, wherein the positioning member is a ring component, and at least one concave structure is arranged on an outer surface of the positioning member.

13. The delivery device according to claim 12, wherein a plurality of concave structures are provided and arranged along the circumferential direction of the positioning member.

14. An intravascular stent system, comprising an intravascular stent and the delivery device according to claim 1, wherein the delivery device delivers the intravascular stent.

15. The intravascular stent system according to claim 14, wherein the delivery device comprises an end socket, a push rod and an outer sheath catheter; the distal end of the inner core tube is connected with the end socket, and a guide wire passes through a tube cavity of the inner core tube.

16. The intravascular stent system according to claim 15, wherein the end socket is located at the distal end of the delivery device, the distal end of the end socket is tapered, and the outer diameter of the distal end of the end socket gradually decreases along a direction from the proximal end to the distal end, so that the end socket can easily enter a blood vessel via percutaneous puncture.

17. The intravascular stent system according to claim 15, wherein the push rod has a tubular structure which surrounds the inner core tube, the push rod is fixedly connected with the inner core tube, and an inner wall of the push rod is fitted to an outer wall of the inner core tube.

18. The intravascular stent system according to claim 17, wherein the distal end of the push rod is located on the proximal side of the distal end of the inner core tube, so that there is an axial clearance between the distal end of the push rod and the proximal end of the end socket, and the inner core tube forms a loading region for the intravascular stent within a longitudinal interval corresponding to the axial clearance.

19. The intravascular stent system according to claim 18, wherein the outer sheath catheter slidably surrounds the inner core tube and the push rod; when the outer sheath catheter slides to the distal end of the delivery device until it abuts against the proximal end of the end socket, the loading region is closed, and the intravascular stent loaded in the loading region is radially compressed.

20. The delivery device according to claim 1, wherein the corrugated rings extend spirally in an axial direction of the intravascular stent.

* * * * *